United States Patent [19]

Uzan et al.

[11] Patent Number: 5,514,330

[45] Date of Patent: May 7, 1996

[54] WASHING HEAD IN AUTOMATIC IMMUNOLOGICAL ASSAY APPARATUS

[75] Inventors: Michel Uzan, Pavillons-sous-Bois; Thierry Gicquel, Courdimanche, both of France

[73] Assignee: Laboratoires Merck-Clevenot, Nogent-sur-Marne, France

[21] Appl. No.: 362,745

[22] Filed: Dec. 22, 1994

Related U.S. Application Data

[63] Continuation of Ser. No. 107,962, Aug. 17, 1993, abandoned.

[30] Foreign Application Priority Data

Sep. 11, 1992 [FR] France ................... 92 10850

[51] Int. Cl.⁶ ........................................... G01N 35/10
[52] U.S. Cl. ..................... 422/64; 422/63; 422/67; 422/100; 422/101; 436/43; 436/47; 436/49; 436/174; 436/177; 436/180; 436/807
[58] Field of Search .................... 422/63–67, 81, 422/100–104; 436/43, 49, 54, 174, 180, 47, 806, 807

[56] References Cited

U.S. PATENT DOCUMENTS

| | | | |
|---|---|---|---|
| 3,951,605 | 4/1976 | Natelson | 422/65 |
| 4,313,735 | 2/1982 | Yamashita et al. | 422/64 X |
| 4,451,433 | 5/1984 | Yamashita et al. | 422/63 |
| 4,635,665 | 1/1987 | Namba et al. | 137/167 R |
| 5,104,808 | 4/1992 | Laska et al. | 436/48 |
| 5,128,103 | 7/1992 | Wang et al. | 422/64 |
| 5,158,895 | 10/1992 | Ashihara et al. | 436/526 |
| 5,183,638 | 2/1993 | Wakatake | 422/64 |
| 5,192,505 | 3/1993 | Sakagami | 422/64 |
| 5,215,714 | 6/1993 | Okada et al. | 422/64 |

FOREIGN PATENT DOCUMENTS

| | | |
|---|---|---|
| 355823 | 2/1990 | European Pat. Off. . |
| 410645 | 1/1991 | European Pat. Off. . |
| 0410645 | 1/1991 | European Pat. Off. . |
| 488247 | 6/1992 | European Pat. Off. . |
| 2655426 | 6/1991 | France . |
| 3402304 | 7/1984 | Germany . |
| WO91/07662 | 5/1991 | WIPO . |

Primary Examiner—Jeffrey R. Snay
Assistant Examiner—Long V. Le
Attorney, Agent, or Firm—Bell, Seltzer, Park & Gibson

[57] ABSTRACT

Automatic apparatus for immunological assay, in which reaction vessels containing samples to be analyzed and reagents are carried by a rotary module which is rotated stepwise, and which is associated with a washing head including needles for sucking up and for injecting liquid for washing magnetic particles in the reaction vessels, and additional needles for sucking up and for injecting a cleaning or washing liquid for the reaction vessels.

10 Claims, 3 Drawing Sheets

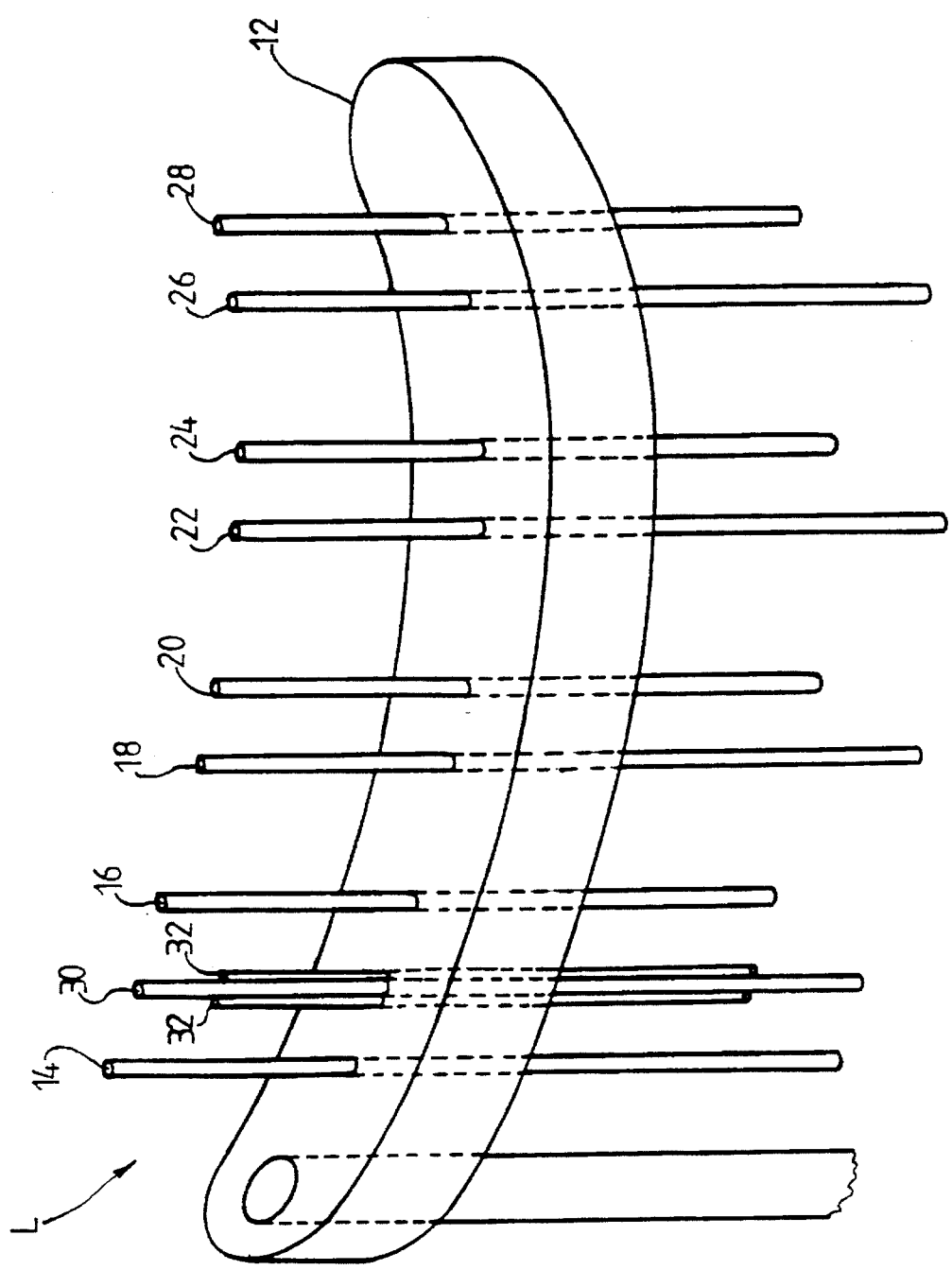

WASHING HEAD IN AUTOMATIC IMMUNOLOGICAL ASSAY APPARATUS

This application is a continuation of application Ser. No. 08/107,962, filed Aug. 17, 1993, now abandoned.

The invention relates to automatic apparatus for immunological assay of at least one substance in a plurality of samples to be analyzed.

BACKGROUND OF THE INVENTION

An apparatus of this type has already been developed by the Applicant and is described, in particular, in PCT International Application published under the number WO91/07662.

In summary, that apparatus comprises:

a sample module comprising a plurality of tubes containing the samples to be analyzed and carried by a rotary turntable or ring;

a reagent module comprising a rotary turntable or ring supporting tubes containing the reagent(s) used for the analyses to be performed, at least one of said reagents being in the form of magnetic particles;

a reaction module comprising a rotary turntable or ring carrying a plurality of tubes or vessels each intended to receive a determined quantity of a sample and a determined quantity of an appropriate reagent, a washing device being associated with said reaction module;

drive means for driving said modules in stepwise rotation;

means enabling the desired quantities of samples and of reagents to be conveyed to the reaction vessels or tubes;

means suitable for reading the results of reactions performed in the reaction vessels or tubes; and a computer system for controlling the various modules and their drive means, to perform a succession of analysis cycles.

Each analysis cycle comprises a series of steps constituting at least one immunological incubation, and a series of steps constituting a developing incubation, in particular an enzymatic incubation, each step corresponding to a number of sequential positions of a reaction vessel or tube in the reaction module, the stop time of a reaction vessel or tube in any one position being constant.

The washing device associated with the reaction module serves to wash the above-mentioned magnetic particles between incubations.

That apparatus has the advantage of enabling ELISA, RIA, FIA, LIA, FPIA, CLIA, etc. techniques to be fully automated and it is particularly applicable to detecting ligands, antiligands, haptens, or any other biological or non-biological substance that may optionally be present in a single sample to be analyzed.

That apparatus also has the following advantages:

it is possible to perform random access multi-parameter assay of samples;

it is possible to obtain a high assay rate (e.g. 100 assays in 50 minutes); and the set of reagents can be calibrated using a multi-parameter calibration agent.

In one embodiment of that apparatus, the reaction module supports four groups of 25 reaction vessels, i.e. a total of 100 vessels, and each complete operating cycle of the apparatus corresponds to processing 100 vessels, i.e. 99 assays and 1 control. At the end of each cycle, the apparatus stops and the operator needs to withdraw the four groups of 25 vessels that have been used, to replace them on the reaction module with four groups of new vessels, to withdraw the tubes containing samples whose assays have just been performed from the sample module and replace them with tubes containing new samples to be analyzed, and to key in a new work list on the control keyboard of the computer system (patient name(s), types of assays to be performed, etc.). Since the groups of vessels are fixed on the rotary turntable of the reaction module, they can be replaced only when the apparatus is fully stopped. Altogether the above operations take up about 15 minutes, thereby slowing down the operating rate of the apparatus in the long run.

In order to avoid stopping the apparatus at the end of each operating cycle, it would naturally be possible to leave the reaction vessels on the reaction module and to associate vessel-cleaning means with the module. Nevertheless, that would require the number of successive positions through which each of the reaction vessels passes to be increased, since cleaning operations must necessarily be performed in a plurality of steps, and that would increase the duration of each operating cycle of the apparatus so no time would be saved.

OBJECTS AND SUMMARY OF THE INVENTION

A particular object of the present invention is to avoid that drawback.

The invention provides an apparatus of the above-specified type in which the vessels carried by the reaction module can be cleaned automatically at the end of each assay, thereby avoiding the need to withdraw them and replace them with new vessels, and to do this without increasing the duration of the operating cycle of the apparatus.

To this end, the invention provides an automatic apparatus for immunological assay of at least one substance in a plurality of samples to be analyzed, the apparatus comprising a rotary module for supporting samples, a rotary module for supporting a plurality of reaction vessels, a rotary module for supporting reagents, at least one of which is in the form of magnetic particles, means for driving the rotary modules stepwise, means enabling desired quantities of samples and of reagents to be conveyed into the reaction vessels, and a washing head associated with the support module for the reaction vessels and including a plurality of groups of injection and suction needles for injecting a washing liquid for said magnetic particles into said vessels and for sucking it up, together with means for applying a magnetic field to said particles in order to keep them in the vessels during the liquid suction stages, the washing head comprising an additional group of injection and suction needles for injecting a vessel-cleaning liquid and for sucking up the contents of the vessels.

The invention thus provides for cleaning the reaction vessels by using the means which were already provided on the apparatus for use during an assay to wash the magnetic particles constituting one of the abovementioned reagents. Under such conditions, it suffices to increase the number of positions provided on the rotary turntable of the reaction module by one unit, and this does not change the total duration of a full operating cycle of the apparatus.

Advantageously, the additional group of injection and suction needles is located on the washing head upstream from the above-mentioned groups of needles for injecting and sucking up the liquid for washing the magnetic particles, "upstream" being relative to the travel direction of the reaction vessels.

Thus, the pre-existing groups of needles for injecting and sucking up a washing liquid for the magnetic particles are also used to complete washing of the reaction vessels.

According to yet another characteristic of the invention, the above-mentioned additional group of injection and suction needles are juxtaposed to act simultaneously in a single reaction vessel.

In this way, the vessel-cleaning liquid is injected into a vessel and is sucked up from said vessel in a single step.

In an embodiment of the invention, the above-mentioned additional group of needles comprises one suction needle and two injection needles whose free ends include means for spraying liquid on the walls of a reaction vessel.

BRIEF DESCRIPTION OF THE DRAWINGS

The invention will be better understood and other characteristics, details, and advantages thereof will appear more clearly on reading the following description given by way of example and made with reference to the accompanying drawings, in which:

FIG. 2 is a diagrammatic perspective view of the washing head used in said apparatus;

FIG. 3 is a diagrammatic view of a needle for injecting a cleaning liquid into a reaction vessel;

MORE DETAILED DESCRIPTION

Figure 1:
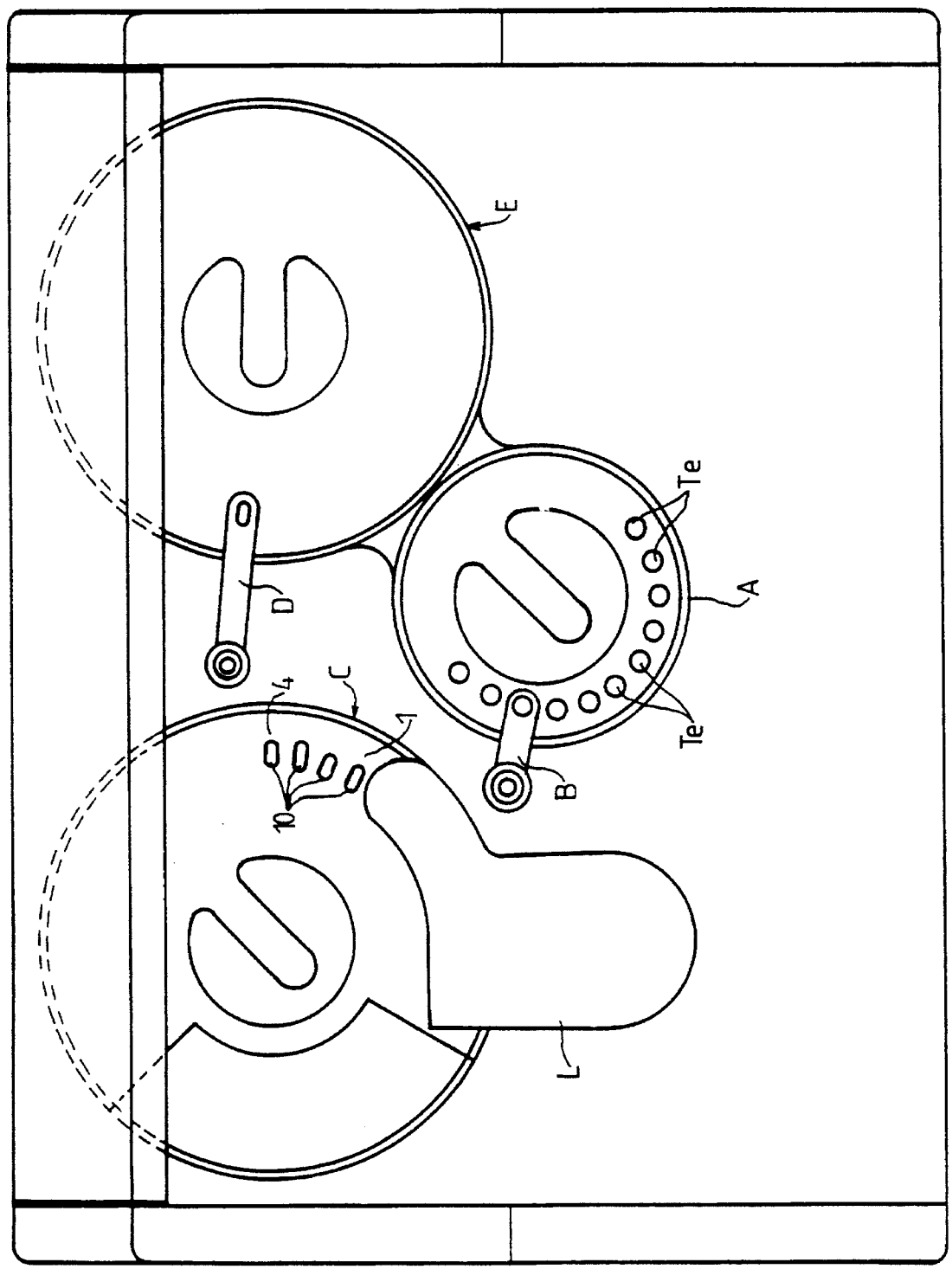
FIG. 1 is a diagrammatic view of an assay apparatus of the invention.

Reference is made initially to FIG. 1 which is a diagram of apparatus of the invention and which corresponds to FIG. 1 of above-mentioned International Application WO91/07662, the contents of which is incorporated herein by reference.

As already described in the above-mentioned international application, this apparatus comprises a sample module A, a reaction module C, and a reagent module E, each module comprising a rotary turntable or ring fitted with supports for tubes or vessels and rotated by an electric motor under the control of a computer system which serves, in particular, to synchronize stepwise rotation of the modules A, C, and E as a function of the assays to be performed.

Sample taking and distributing means B are provided between the sample module A and the reaction module C for the purpose of taking desired quantities of samples to be analyzed from the sample tubes Te carried by the sample module A, and for distributing them in the reaction vessels 10 carried by the reaction module C as said vessels follow one another through the position numbered 1 in the drawing.

Means D for taking and distributing reagent are provided between the reagent module E and the reaction module C for the purpose of taking desired quantities of reagent and distributing them in the reaction vessels 10 as they pass through the position numbered 4 in the drawing.

A washing head L is associated with the reaction module C and comprises groups of needles for sucking up and injecting liquid in the reaction vessels, as they pass through a certain number of successive angular positions. The needles are carried by a support that is guided in vertical displacement and that is associated with means for driving them with reciprocating vertical motion, in order to lower the needles into the reaction vessels and to raise them above said vessels.

As can be seen in the diagram of FIG. 2, and as already described in the above-mentioned international application, this support 12 comprises a first needle 14 for sucking up liquid in a reaction vessel, said first needle 14 being followed in the travel direction of the reaction vessels as represented by arrow F, by a needle 16 for injecting a washing solution, a needle 18 for sucking up liquid, a needle 20 for injecting the washing solution, a needle 22 for sucking up liquid, a needle 24 for injecting the washing solution, a needle 26 for sucking up liquid, and a needle 28 for injecting a substrate.

The washing solution injected by the needles 16, 20, and 24 is intended to wash magnetic particles constituting a reagent during an assay. The suction needles 18, 22, and 26 are used for sucking said washing solution out of the reaction vessels, while the magnetic particles constituting the reagent are held by magnetic attraction against the walls of the reaction vessels under the effect of a magnetic field generated by permanent magnets permanently disposed on either side of the path followed by the reaction vessels, as described in greater detail with reference to FIG. 4.

The last needle 28 of the washing head serves to inject a substrate into the reaction vessels, e.g. alkaline phosphatase (PNPP) for enzyme incubation prior to reading the result of the assay.

The distance between two successive needles on the washing head naturally corresponds to one rotary step of the reaction module, or to a multiple thereof. In particular, it can be seen that the needles 18 and 20 are separated by a distance equal to one rotary step whereas needles 20 and 22 are separated by a distance equal to twice the rotary step.

In accordance with the present invention, the support 12 includes an additional group of needles for injecting and sucking up liquid, which needles are used for cleaning the reaction vessels after assays have been performed. This additional group of injection and suction needles comprises at least one suction needle and at least one injection needle, and in the example shown in FIG. 2, it comprises a suction needle 30 and two injection needles which are juxtaposed to act in the same reaction vessel stopped in a determined angular position of the reaction module. In addition, as shown diagrammatically in FIG. 3, the bottom end of each injection needle 32 may be split into a fork so as to form two nozzles 34 for spraying liquid on the inside walls of a reaction vessel.

This additional group of needles 30, 32 is interposed between the first liquid suction needle 14 and the first needle 16 for injecting a washing solution, and it is at a distance from the needles 14 and 16 that is equal to one rotary step of the reaction module.

Figure 4:
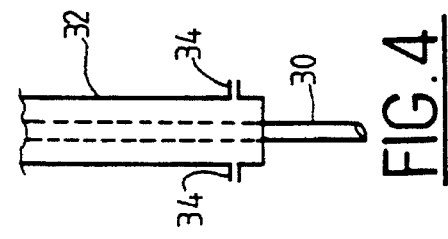

In the variant embodiment of FIG. 4, the additional needle group comprises a suction needle 30 and an injection needle 32 that are coaxial, the suction needle 30 extending inside the injection needle 32 whose bottom end includes lateral nozzles 34 pointing towards the walls of the reaction vessels.

Figure 5:
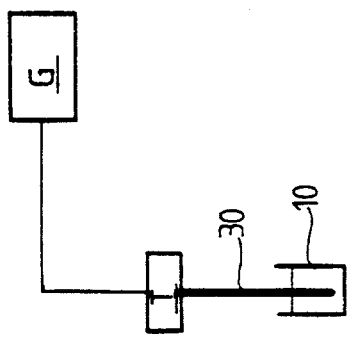
FIGS. 4 and 5 show two variant embodiments of needles for cleaning the vessels.

In addition, in order to facilitate removal of magnetic particles from the walls of the vessels so as to put them back into suspension in the cleaning liquid, it is advantageous to apply an ultrasound field to them, e.g. via the suction needle. To do this, and as shown diagrammatically in FIG. 5, an AC generator G is used whose output is connected to a transducer T secured to the suction needle 30. Plunged into the cleaning liquid contained in a reaction vessel 10, this needle behaves like a "sonotrode" propagating ultrasound into the cleaning liquid. The frequency of the ultrasound may lie in the range about 1 kHz to about 50 MHz, and the power thereof may lie in the range 1 mW to 50 W, for example.

Figure 6:
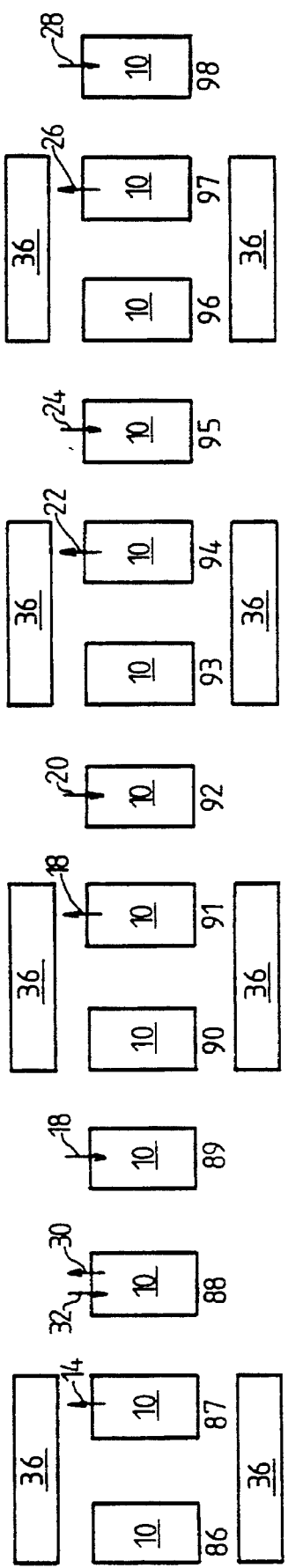
FIG. 6 is a diagram showing the various steps involved in cleaning the reaction vessels at the end of assay.

Operation is now explained with reference to FIG. 6 which reproduces substantially the same reference numerals as in the above-mentioned international application for the successive positions occupied by the reaction vessels, in order to facilitate understanding.

In position No. 1 (not shown in FIG. 6), a quantity of sample to be analyzed is placed in a reaction vessel 10 that has been brought into said position by rotation of the reaction module.

In position 4 (not shown in FIG. 6), a quantity of a reagent constituted by magnetic particles is disposed in said vessel. These magnetic particles are coupled to a binder specific to the substance to be detected in the sample to be analyzed.

The sample and the reagent remain in contact for an appropriate length of time as determined by the stepwise rotation of the reaction module between positions 4 and 86.

Two permanent magnets 36 are disposed on either side of the reaction vessels in positions 86 and 87 to act by magnetic attraction on the magnetic particles constituting the reagent, so as to hold these magnetic particles against the walls of the reaction vessels. The magnetic particles are thus subjected to premagnetization in position 86 and then to additional magnetization in position 87. Furthermore, in position 87, the washing head is lowered and the liquid contained in the reaction vessel is sucked up by the needle 14, leaving the magnetic particles held against the walls of the reaction vessel.

In position 88 which is reached during the first complete rotation of the reaction module, nothing takes place: the needles 30 and 32 are lowered by the washing head into the reaction vessel, but they are not operative, the magnetic particles remain held against the walls of the reaction vessel, and therefore run no risk of contaminating the needles 30 and 32.

In position 89, a magnetic particle washing solution is injected into the reaction vessel by needle 16.

In the following positions 90 and 91, there are two more permanent magnets 36 applying magnetic attraction to the magnetic particles of the reagent to hold them against the walls of the reaction vessel. As before, premagnetization takes place in position 90 and additional magnetization takes place in position 91. In this position, the liquid contained in the reaction vessel is sucked up by the needle 18.

The same operations of injecting a washing solution for the magnetic particles are repeated in positions 92 and 95, with the operations of premagnetization and of additional magnetization by permanent magnets 36 being repeated in positions 93 and 94, and in positions 96 and 97, respectively. The operations of sucking up the washing liquid are repeated in positions 94 and 97, using the needles 22 and 26, respectively.

The reaction vessel is then brought to position 98 where it receives a quantity of substrate injected by the needle 28.

The substrate and the reagent remain in contact for a length of time appropriate for enzyme incubation, and until the reaction vessel reaches a position 83 where the assay result is read after premagnetization performed in position 82 to hold the magnetic particles against the walls of the reaction vessel.

By rotating the reaction module, the reaction vessel is then brought again to position 86 when the magnetic particles are subjected to premagnetization, and then to position 87 where they are subjected to additional magnetization, and where the liquid contained in the reaction vessel is sucked up by the needle 14.

In the following position 88, a washing or cleaning solution for the reaction vessel is injected into said vessel by the needle(s) 32 whose nozzles 34 spray jets of liquid against the walls of the vessel, and preferably in the vicinity of the corners thereof so as to set up a turbulent flow of liquid in the vessel, thereby enabling the magnetic particles to be put back into suspension since they are no longer subjected to the magnetic field produced by the magnets 36 in positions 86 and 87, which means they can be removed from the walls.

The magnetic particles are preferably also subjected at this moment to the ultrasound field produced by the generator G, the transducer T, and suction needle 30 in the liquid contained in the vessel 10.

Simultaneously, the washing or cleaning liquid into which the magnetic particles have been put back into suspension is sucked up and disposed of by means of the needle 30.

In the following position 89, a washing solution is again injected into the reaction vessel by the needle 16 so as to complete the cleaning performed in position 88, after which it is sucked up from said vessel by the needle 18 in position 91. These operations of injecting the washing solution and of sucking it up are again repeated in positions 92 and 94, and then in positions 95 and 97. Rotation of the reaction module then returns the reaction vessel to position 1 where it can receive a quantity of a new sample to be analyzed.

The above description relates to the operation of the apparatus when performing a one-reagent assay (e.g. HCG, prolactin, etc.). When a two-reagent assay is performed (Toxo G, chlamydia, rubella, etc.), the reaction module performs one more complete revolution, the first revolution being used for performing the first reaction by means of a first reagent constituted by magnetic particles, the second revolution serving to perform a second reaction by means of a second reagent or conjugate, the third revolution serving for enzyme incubation, reading the result, and cleaning the reaction vessels.

The essential steps of operation of the apparatus of the invention when performing single-reagent assays and two-reagent assays are recalled in the following table:

| REACTION POSITIONS | ONE-REAGENT ASSAY | TWO-REAGENT ASSAY |
|---|---|---|
| 1st revolution | Particle Washing | Particle Washing |
| 1 | Deposit sample | Deposit sample |
| 4 | Deposit single reagent | Deposit reaction R1 |
| 86 | Premagnetization | Premagnetization |
| 87 | Magnetization-suction | Magnetization-suction |
| 88 | | |
| 89 | Washing | Washing |
| 90 | Premagnetization | Premagnetization |
| 91 | Magnetization-suction | Magnetization-suction |
| 92 | Washing | Washing |
| 93 | Premagnetization | Premagnetization |
| 94 | Magnetization-suction | Magnetization-suction |
| 95 | Washing | Washing |
| 96 | Premagnetization | Premagnetization |
| 97 | Magnetization-suction | Magnetization-suction |
| 98 | Deposit substrate | |
| 2nd revolution | Vessel Washing | Particle Washing |

| REACTION POSITIONS | ONE-REAGENT ASSAY | TWO-REAGENT ASSAY |
|---|---|---|
| 4 | | Deposit reagent R2 |
| 82 | Premagnetization | |
| 83 | Read result | |
| 86 | Premagnetization | Premagnetization |
| 87 | Magnetization suck up supernatant | Magnetization-suction |
| 88 | Suck up particles | |
| 89 | Washing | Washing |
| 90 | Premagnetization | Premagnetization |
| 91 | Magnetization-suction | Magnetization-suction |
| 92 | Washing | Washing |
| 93 | Premagnetization | Premagnetization |
| 94 | Magnetization-suction | Magnetization-suction |
| 95 | Washing | Washing |
| 96 | Premagnetization | Premagnetization |
| 97 | Magnetization-suction | Magnetization-suction |
| 98 | | Deposit substrate |
| 3rd revolution | | Vessel washing |
| 1 | Deposit a new sample | |
| 4 | Deposit a new reagent | |
| 82 | | Premagnetization |
| 83 | | Read result |
| 86 | | Premagnetization |
| 87 | | Magnetization-suction of supernatant |
| 88 | | Suction of particles |
| 89 | | Washing |
| 90 | | Premagnetization |
| 91 | | Magnetization-suction |
| 92 | | Washing |
| 93 | | Premagnetization |
| 94 | | Magnetization-suction |
| 95 | | Washing |
| 96 | | Premagnetization |
| 97 | | Magetization-suction |
| 1 | | Deposit a new sample |
| 4 | | Deposit a new reagent |

In general, the invention makes the following possible:

continuous operation of the assay apparatus;

a non-negligible saving of time by making it possible to begin new assays as soon as the second revolution of the reaction module has been completed when performing single-reagent assay and by eliminating the prior art requirements to stop the apparatus during a length of time sufficient for replacing the used reaction vessels, replacing the assayed samples with new samples, and keying information into the computer system concerning the assays to be performed on the new samples, with the last two operations being performed, in the present invention, while the previously requested assays are being terminated; and obtaining savings in reaction vessels which were generally discarded after a single use in the prior art.

In a variant of the invention, the enzyme incubation step may be omitted and replaced by depositing a luminescent or chemico-luminescent marker in the reaction vessel and then immediately reading the result, thus making it possible to omit the second revolution of the reaction module when using a one-reagent assay or the third revolution of said module when using a two-reagent assay. It is then advantageous to dispose the additional group of injection and suction needles on the washing head downstream from the needles normally used for washing the magnetic particles, instead of placing them upstream from said needles.

We claim:

1. Automatic apparatus for immunological assay of at least one substance in a plurality of samples to be analyzed, the apparatus comprising a rotary module for supporting samples, a rotary module for supporting a plurality of reaction vessels, a rotary module for supporting reagents, at least one of which is in the form of magnetic particles, means for driving the rotary modules stepwise in a rotation direction, means enabling desired quantities of samples and of reagents to be conveyed into the reaction vessels, magnetic particles washing means comprising a washing head associated with the rotary module for the reaction vessels and a plurality of injection and suction needles for injecting a washing liquid for said magnetic particles into said vessels and for sucking up the washing liquid, and vessel cleaning means associated with the rotary module for the reaction vessels said vessel cleaning means comprising at least some of the same injection and suction needles used by said magnetic particles washing means and an additional group of injection and suction needles for injecting a vessel-cleaning liquid into the vessels and for sucking up the cleaning liquid from the vessels, said additional group being mounted on said washing head adjacent to said injection and suction needles of the magnetic particles washing means.

2. Apparatus according to claim 1, wherein the additional group of injection and suction needles is located on the washing head upstream from the above-mentioned groups of needles for injecting and sucking up the liquid for washing the magnetic particles, upstream being relative to the rotation direction of the reaction vessels.

3. Apparatus according to claim 1, wherein the additional group of injection and suction needles is located on the washing head downstream from a first needle for sucking up liquid from the vessels, downstream being relative to the rotation direction thereof.

4. Apparatus according to claim 1, wherein the additional group of needles is located on the washing head downstream from the above-mentioned groups of needles for injecting and sucking up the washing liquid for the magnetic particles, downstream being relative to the rotation direction of the reaction vessels.

5. Apparatus according to claim 1, wherein the additional group of needles include at least one suction needle and at least one injection needle whose free end includes means for spraying liquid on walls of the vessels.

6. Apparatus according to claim 1, wherein the suction and injection needles of the above-mentioned additional group are juxtaposed to act simultaneously in a single reaction vessel.

7. Apparatus according to claim 1, wherein the suction and injection needles of the additional group are coaxial, the suction needle being contained inside the injection needle and extending beyond a free end thereof.

8. Apparatus according to claim 1, including means for applying an ultrasound field to the magnetic particles to put them back into suspension in the vessels, said means comprising an AC generator connected to a transducer secured to the suction needle of the above-mentioned additional group.

9. Apparatus according to claim 1, wherein said apparatus operates continuously.

10. Apparatus according to claim 1 further comprising means for applying a magnetic field to said magnetic particles in the vessels.

* * * * *